United States Patent
Carr et al.

[11] Patent Number: 5,541,201
[45] Date of Patent: Jul. 30, 1996

[54] ANTIARRHYTHMIC PIPERIDIN-1-YL-2,2-DIALKYLPROPANONE ARYLSULFONAMIDE DERIVATIVES

[75] Inventors: Albert A. Carr; Richard C. Dage; David A. Hay; John E. Koerner; Tung Li, all of Cincinnati, Ohio

[73] Assignee: Merrell Pharmaceuticals, Inc., Cincinnati, Ohio

[21] Appl. No.: 460,029

[22] Filed: Jun. 2, 1995

Related U.S. Application Data

[63] Continuation of Ser. No. 324,870, Oct. 18, 1994, abandoned, which is a continuation of Ser. No. 171,882, Dec. 22, 1993, abandoned, which is a continuation of Ser. No. 81,762, Jun. 23, 1993, abandoned.

[51] Int. Cl.$^6$ .......... A61K 31/445; C07D 211/32
[52] U.S. Cl. .......... 514/330; 514/331; 546/225; 546/232; 546/235
[58] Field of Search .......... 546/225, 232, 546/235; 514/330, 331

[56] References Cited

U.S. PATENT DOCUMENTS

| | | | |
|---|---|---|---|
| 4,876,262 | 10/1989 | Oinuma | 514/318 |
| 4,996,215 | 2/1991 | Oinuma | 514/316 |
| 5,118,689 | 6/1992 | Oinuma | 514/300 |
| 5,179,095 | 1/1993 | Oinuma | 514/249 |

FOREIGN PATENT DOCUMENTS

WO9118603  12/1991  WIPO .

*Primary Examiner*—Ceila Chang
*Attorney, Agent, or Firm*—J. Michael Dixon

[57] ABSTRACT

The invention is directed to a new class of antiarrhythmic agents of the formula:

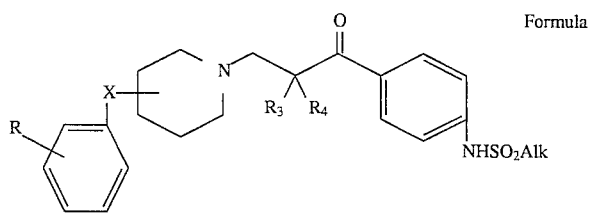

Formula in which R is represented by hydrogen, halogen, $C_{1-4}$ alkyl, $C_{1-4}$ alkoxy, $CF_3$, $SR_1$, $NHC(O)R_2$, $NH_2$, or $OH$; $R_1$ is hydrogen or $C_{1-4}$ alkyl; $R_2$ is $C_{1-4}$ alkyl; X is represented by CO or CHOH; $R_3$ and $R_4$ are each independently represented by methyl, ethyl, n-propyl, or $R_3$ and $R_4$ together with the carbon atom to which they each are attached form a $C_5$ or $C_6$ cycloalkyl; and Alk is a $C_{1-4}$ alkyl; or a pharmaceutically acceptable addition salt thereof.

3 Claims, No Drawings

ANTIARRHYTHMIC PIPERIDIN-1-YL-2,2-DIALKYLPROPANONE ARYLSULFONAMIDE DERIVATIVES

This is a continuation of application Ser. No. 08/324,870, filed Oct. 18, 1994, now abandoned, which is a continuation of application Ser. No. 08/71,882, filed Dec. 22, 1993, now abandoned, which is a continuation of application Ser. No. 08/081,762, filed Jun. 23, 1993, now abandoned, herein incorporated by reference.

The present invention is directed to a new class of piperidin-1-yl-2,2-dialkylpropanonearylsulfonamide derivatives which are useful as Class III antiarrhythmic agents. Another aspect of the invention is directed to a method for treating cardiac arrhythmias. An additional aspect of the invention is directed to pharmaceutical compositions containing these compounds.

In accordance with the present invention a new class of antiarrhythmic agents have been discovered which can be described by the following formula:

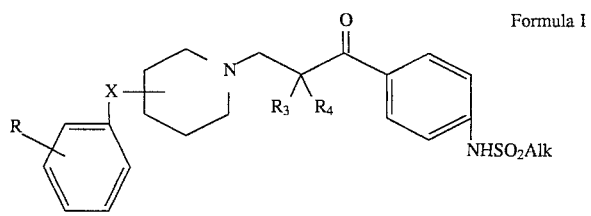

Formula I in which R is represented by hydrogen, halogen, $C_{1-4}$ alkyl, $C_{1-4}$ alkoxy, $CF_3$, $SR_1$, $NHC(O)R_2$, $NH_2$, or OH; $R_1$ is hydrogen or $C_{1-4}$ alkyl; $R_2$ is $C_{1-4}$ alkyl; X is represented by CO or CHOH; $R_3$ and $R_4$ are each independently represented by methyl, ethyl, n-propyl, or $R_3$ and $R_4$ together with the carbon atom to which they each are attached form a $C_5$ or $C_6$ cycloalkyl; and Alk is a $C_{1-4}$ alkyl; and the pharmaceutically acceptable addition salts thereof.

As used in this application:

a) the term "halogen" refers to a fluorine, chlorine, or bromine atom;

b) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc.;

c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;

d) the term "CO" refers to a carbonyl group having the following structure:

e) the term "CHOH" refers to a hydroxymethylene group;

f) the term "$C_5$ and $C_6$ cycloalkyl" refers to cyclopentyl and cyclohexyl:

the term "pharmaceutically acceptable addition salt" refers to either an acid addition salt or a basic addition salt.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethane sulfonic acid. Either the mono- or di-acid salts may be formed, and such salts may exist in either a hydrated or substantially anhydrous form.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, or potassium, and aliphatic or alicyclic amines, such as methylamine, dimethylamine, or trimethylamine. Either the mono- or di-basic salts may be formed with those compounds.

Since $R_3$ and $R_4$ can be different alkyl substituents some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases, resolution via chiral salt formation and subsequent separation by selective crystallization or ester formation from a chiral acid followed by separation of the resultant diastereomeric esters and hydrolysis to the desired enantiomer.

The X substituent may be bonded to either the 3-position or the 4-position of the piperidinyl ring. The phenyl ring adjacent to the 3- or 4-position of the piperidinyl ring may be optionally substituted. It is possible for this phenyl ring to contain up to 3 non-hydrogen substituents. These substituents can be located at any of the ortho, meta or para positions. These substituents can be the same or different.

To further illustrate the present invention the compounds in which $R_3$ and $R_4$ together with the carbon atom to which they each are attached form a $C_5$ or $C_6$ cycloalkyl are depicted below:

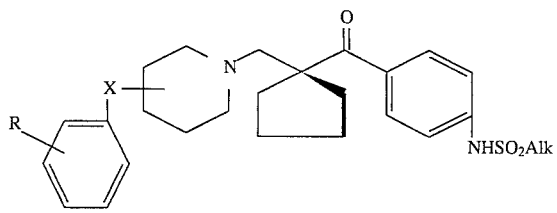

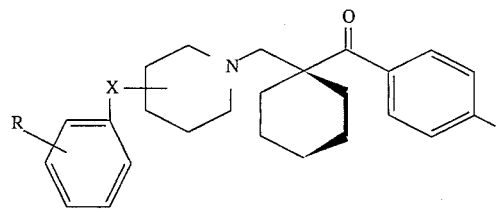

Illustrative Examples of compounds encompassed by the present invention include:

N-[4-[3-[4-(3,4-difluorobenzoyl)piperidin-1-yl]-1-oxo-2,2-dimethylpropane]phenyl]methanesulfonamide, N-[4-[3-[4-(4-fluorobenzoyl)piperidin-1-yl]-1-oxo-2,2-dimethylpropane]phenyl]methanesulfonamide, N-[4-[3-[4-(2,3-dimethoxybenzoyl)piperidin-1-yl]-1-oxo-2,2-dimethylpropane]phenyl]methanesulfonamide, N-[4-[3- [4-(2,4,6-trimethylbenzoyl)piperidin-1-yl]-1-oxo-2,2-dimethylpropane]phenyl]methanesulfonamide, N-[4-[[3-[4-(methylthio)benzoyl]piperidin-1-yl]-1-oxo-2,2-dimethylpropane]phenyl]methanesulfonamide, N-[4-[3-[4-(2-ethoxybenzoyl)piperidin-1-yl]-1-oxo-2,2-dimethylpropane]phenyl]methanesulfonamide, N-[4-[3-[4-(4-chlorobenzoyl)piperidin-1-yl]-1-oxo-2,2-dimethylpropane]phenyl]methanesulfonamide, N-[4-[3-[4-(4-aminobenzoyl)piperidin-1-yl]-1-oxo-2,2-dimethylpropane]phenyl]methanesulfonamide, N-[4-[3-[4-(4-acetylaminobenzoyl)piperidin-1-yl]-1-oxo-2,2-dimethylpropane]phenyl]methanesulfonamide, N-[4-[3-[4-(4-fluorobenzoyl)piperidin-1-yl]-1-oxo-2,2-diethylpropane]phenyl]methanesulfonamide, N-[4-[3-[4-(3,4-difluorobenzoyl)piperidin-1-yl]-1-oxo-2,2-spirocyclohexylpropane]phenyl]methanesulfonamide, N-[4-[3-[4-(3,4-difluorobenzoyl)piperidin-1-yl]-1-oxo-2,2-spirocyclopentylpropane]phenyl]methanesulfonamide, N-[4-[3-[4-(3,4-difluorobenzoyl)piperidin-1-yl]-oxo-2,2-dipropylpropane]phenyl]methanesulfonamide, N-[4-[3-[4-[(4-fluorophenyl)hydroxymethyl]piperidin-1-yl]-1-oxo-2,2-dimethylpropane]phenyl]methanesulfonamide, N-[4-[3-[3-[(3,4-difluorophenyl)hydroxymethyl]piperidin-1-yl]-1-oxo-2,2-dimethylpropane]phenyl]methanesulfonamide, N-[4-[3-[3-[(4-fluorophenyl)hydroxymethyl]piperidin-1-yl]-1-oxo-2,2-dimethylpropane]phenyl]methanesulfonamide, N-[4-[3-[3-(4-fluorobenzoyl)piperidin-1-yl]-1-oxo-2,2dimethylpropane]phenyl]methanesulfonamide, The compounds of Formula I can be prepared using techniques which are analogously known in the art. One method for preparing these compounds is illustrated below Reaction Scheme I:

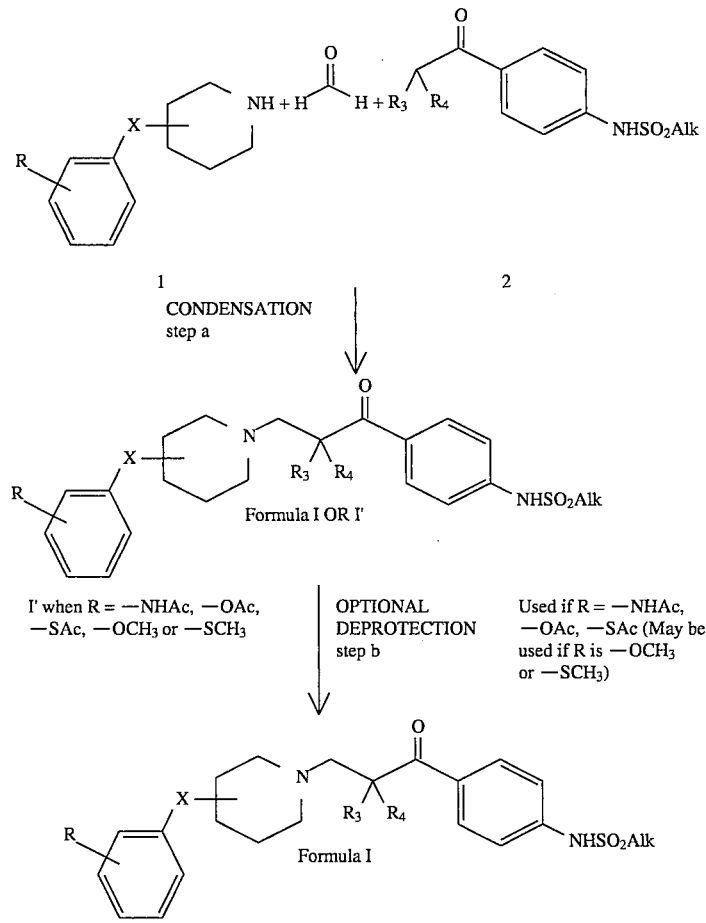

REACTION SCHEME 1

I' when R = —NHAc, —OAc, —SAc, —OCH₃ or —SCH₃

OPTIONAL DEPROTECTION step b

Used if R = —NHAc, —OAc, —SAc (May be used if R is —OCH₃ or —SCH₃)

In step a of Reaction Scheme I, an condensation reaction is carried out between a 3-or 4-substituted piperidine as described by structure 1, in which R and X are as in Formula I with the proviso that when R is to be OH, SH, or NH₂, then the corresponding acetyl derivative is utilized (i.e., OAc, NHAc, or SAc), and an N-alkylsulfonamidoarylketone as described by structure 2, in which Alk are as in Formula I and formaldehyde or an appropriate formaldehyde equivalent. If R is an acetyl derivative, then it is necessary to carry out the optional Deprotection Reaction of step b which removes any acetyl function which leaves an OH, SH, or $NH_2$ substituent on the molecule.

The appropriate piperidine compound of structure 1 to utilize is one in which X and R are represented by the same substituent as is desired in the final product of Formula I or in which the substituent R is further substituted with an appropriate protecting group. X should be bonded to the 3- or 4- position as is desired in the final product. The appropriate N-alkylsulfonamidoarylketone of structure 2 is one in which Alk is the same substituent as is desired in the final product. The appropriate formaldehyde equivalent is one that performs like formaldehyde in the condensation reaction, such as paraformaldehyde or polyoxymethylene.

The condensation, the Mannich reaction, can be carried out using techniques well known in the art (Modern Synthetic Reactions, H. O. House, Second Edition, W. A. Benjamin Inc.; pages 654–660 and references sited therein). Approximately equivalent amounts of the piperidine compound of structure 1, the N-alkylsulfonamidoarylketone of structure 2, and several portions of a slight excess of formaldehyde or an appropriate formaldehyde equivalent are contacted over the course of the reaction in a solvent such as acetic acid, ethanol, or water. The reaction is typically carried out at a temperature range of from room temperature to reflux for a period of time ranging from 1 hour to 2 days.

The crude product of Formula I or I' can be recovered from the reaction medium and purified by techniques known in the art. For example, the crude compounds can be recovered by organic solvent extraction in the presence of water. Suitable extraction solvents include ethyl acetate, dichloromethane or chloroform. The resulting crude material can then be purified by recrystallization from a solvent system such as methanol, methanol/butanone, isopropanol or chloroform, etc. The compounds may also be purified by chromatographic techniques such as silica gel chromatography. Suitable chromatographic solvents include ethyl acetate, acetone, ethyl acetate/hexane, or ethyl acetate/acetone.

The Optional Deprotection Reaction of step b can also be carried out using techniques known in the art. Typically the crude product of Formula I' in which X is CO is subjected to an acidic hydrolysis with a mineral acid such as HCl (about 0.1–0.5N in methanol). The hydrolysis is typically carried out at a temperature range of from 0° to 30° C. for a period of time ranging from 0.5 to 5 hours. If X is represented by CHOH, then a mild organic acid such as tartaric acid should be utilized. Typically a slight molar excess of the organic acid is utilized in a solvent such as aqueous THF at a temperature of about 0° C. for about 0.5 hours. After either hydrolysis is completed, the reaction medium is neutralized with a mild base such as sodium bicarbonate. The resulting compound of Formula I can be recovered and purified by the same methods taught in step a of Reaction Scheme I.

Methods for producing the 3- and 4-substituted piperidines of structure 1 are known in the art (PCT Application. International Publication No. WO 91/18603; Dec. 12, 1991, U.S. application Ser. No. 534,784, filed Jun. 7, 1990, hereby incorporated by reference.

Methods for producing N-alkylsulfonamidoarylketones of structure 2 are known analogously in the art, by Friedel-Crafts reaction between the appropriate N-alkylsulfonamidobenzene and the appropriate activated acyl compound, as illustrated below in Reaction Scheme 2. The appropriate N-alkylsulfonamidobenzene is one in which Alk is represented by the same substituent as is desired in the final product. The appropriate activated acyl compound is one in which $R_3$ and $R_4$ are as is desired in the final product.

REACTION SCHEME 2

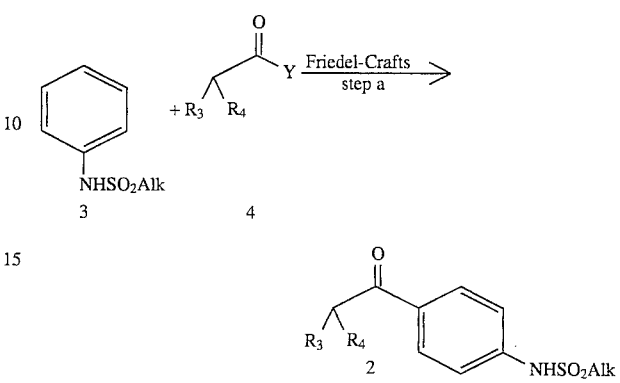

In step a of Reaction Scheme 2, an appropriate N-alkylsulfonamidobenzene of structure 3 and an appropriate activated acyl compound of structure 4 are contacted under the general conditions of the Friedel-Crafts reaction using a suitable Lewis acid. The reaction is carried out in a solvent, such as carbon disulfide, dichloromethane, nitromethane, 1-nitropropane, diethyl ether, n-hexane, acetonitrile, 1,2-dichloroethane, nitrobenzene, or tetrachloroethane with dichloromethane being the preferred solvent. The reaction time varies from about 0.5 hour to 24 hours. The reaction temperature varies from 0° C. to 60° C. An appropriate activated acyl compound of structure 4 are compounds in which Y may be OH, Cl or an anhydride of the acid of compound of structure 4. The N-alkylsulfonamidoarylketone of structure 2 is recovered from the reaction zone by an aqueous quench followed by extraction as is known in the art. The N-alkylsulfonamidoarylketone of structure 2 may be purified by procedures well known in the art, such as chromatography on silica gel using a suitable eluent, such as ethyl acetate and mixtures of ethyl acetate and hexane, and recrystallization from a solvent system such as methanol, methanol/butanone, isopropanol or chloroform, etc.

Suitable Lewis acids for the Friedel-Crafts reaction described in Reaction Scheme 2 step a, are well known and appreciated in the art. Examples of suitable Lewis acids are boron trichloride, aluminum chloride, titanium tetrachloride, ferric chloride, boron trifluoride, tin tetrachloride, cobalt(II)chloride and zinc chloride, with aluminum chloride being preferred. The selection and utilization of suitable Lewis acids for the Friedel-Crafts reaction described in Reaction Scheme 2 step a, is well known and appreciated by one of ordinary skill in the art.

The compounds of Formula I are useful as cardiac antiarrhythmic agents. They can be administered to a patient suffering from an arrhythmic episode in order to terminate that episode and return the myocardium to a normal sinus rhythm. The compounds can also be administered on a prophylactic basis to prevent the occurrence of arrhythmic episodes.

The compounds of Formula I increase the duration of the action potential of myocardial tissue producing an increase in the refractory period of that tissue. Thus, under the classification system of Vaughan Williams these compounds exhibit a Class III antiarrhythmic activity.

One method of demonstrating the antiarrhythmic activity of these compounds is the following test protocol. This protocol demonstrates what effect a compound has upon the action potential of isolated cardiac tissue, such as a Purkinje fiber, an atrial or ventricular trabecular muscle from a dog heart, or a papillary muscle from a guinea pig heart.

Purkinje fibers or trabecular muscles are obtained from either of the ventricles of an anesthetized mongrel dog. Trabecular muscles from either of the atria may also be utilized. Alternatively, papillary muscles are obtained from the right cardiac ventricle of a guinea pig. An appropriate cardiac muscle fiber is then placed in a tissue bath which is continuously perfused with modified Tyrode's solution. The modified Tyrode's solution has the following composition (in mM): NaCl 127.0, KCl 5.4, $NaH_2PO_4$ 0.5, $MgCl_2$ 1.0, $NaHCO_3$ 23.8, $CaCl_2$ 1.8 and glucose 11.1. A gas mixture comprised of 95% $O_2$ and 5% $CO_2$ is bubbled through the solution while it is maintained within a pH range of from 7.3–7.4.

The electrophysiology of the cardiac tissue is monitored by conventional glass microelectrodes. One microelectrode is inserted into a cell in the cardiac muscle fiber and a ground electrode is positioned in the tissue bath. A conventional oscilloscope is utilized to visualize the action potential waveforms of the cardiac cell.

The cardiac muscle fiber is electrically stimulated at a frequency of 0.5 Hz to 3 Hz through a pair of platinum plates placed in the tissue bath. This stimulation is continued for approximately 1 hour in order to allow the electrophysiological characteristics of the fiber to stabilize.

After approximately 1 hour, the fiber should be exhibiting a stable action potential as demonstrated by the waveform displayed on the oscilloscope. At this point, representative control action potentials are recorded and analyzed by a computer.

After establishing a control action potential, the test compound is introduced into the Modified Tyrode's solution in a quantity such that the test compound is present within the tissue bath in a range of from $10^{-8}$ to $10^{-5}$ moles/liter. After the effect of the test compound has reached a steady state, the action potential is again recorded and analyzed in the manner described above.

The in vivo antiarrhythmic activity of the compounds can be demonstrated in the following manner. Mongrel dogs of either sex are anesthetized with sodium pentobarbitol (35 mg/kg, i.v.). The dogs are respirated and the heart is exposed via a thoracotomy. Two pairs of plunge electrodes are placed in the mid-myocardium of the left ventricle for introduction of ventricular extra-stimuli. Two additional pairs of plunge electrodes are placed in the mid-myocardium within 1–2 mm of the ventricular pacing electrodes for recording local bipolar ventricular electrograms. Bipolar electrograms are recorded with the low and high frequency cutoffs set at 30 and 90 Hz, respectively. A pair of stainless steel electrodes are sutured onto the right atrial appendage for pacing the heart. The sinoatrial node is inactivated, and the heart is paced at 150 beats per minute (5 msec duration, twice diastolic threshold voltage or current). The local bipolar electrogram, as well as the Lead II ECG, is recorded continuously on a polygraph, and also acquired by a computer.

Ventricular effective refractory period (ERP) is determined by introduction of a single ventricular extrastimulus (4 msec duration, twice diastolic threshold voltage or current) at progressively shorter delays after the right atrial stimulus, until a propagated ventricular depolarization is not seen in the Lead II ECG.

The ERP is defined as the longest interval between the ventricular extrastimulus that does not result in a propagated ventricular depolarization, and the preceding ventricular depolarization. The ERP is measured by the computer using the local bipolar electrogram from the site adjacent to ventricular stimulating electrodes. ERP's are determined at two sites in each heart and the values averaged. ERP's are initially determined under pretreatment conditions. Test compound is then administered either intravenously via a cannula placed in the right femoral vein, or intraduodenally via a cannula placed in the duodenum. ERP's are redetermined following the administration of that compound. The compounds of Formula I will increase the ERP.

The compounds of the present invention having Class III antiarrhythmic properties are useful for treating a variety of arrhythmic conditions of the heart. Representative examples of arrhythmic conditions which are amendable to treatment with the compounds of the present invention include supraventricular arrhythmias such as atrial tachycardia, atrial flutter, atrial fibrillation and paroxysmal supraventricular tachycardia, and ventricular arrhythmias such as premature ventricular complexes, and life threatening ventricular arrhythmias such as ventricular tachycardia, or ventricular fibrillation. These compounds will also prevent recurrent episodes of the arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, the presence of other underlying disease states, and the particular compound utilized. However as a general guideline, if the compound is being administered orally, then it is preferably administered within a dosage range of from about 0.1 to about 100 mg/kg of patient body weight/day. Likewise, if the compound is being administered parenterally then it is preferably administered within a dosage range of from about 0.01 to about 10.0 mg/kg of patient body weight/day.

Repetitive daily administration may be desirable. Typically, the compounds will be administered from 1–4 times daily. They can also be administered as a continuous drip in critical care environments. The patient's response to the compound can be monitored via an EKG or any other technique conventionally used in the art.

As used in this application:

a) the term "arrhythmia" refers to any variation from the normal rhythm of the heart beat, and;

b) the term "antiarrhythmic" refers to a compound capable of either preventing or alleviating an arrhythmia.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, n-saline, dextrose solutions, fructose solutions, ethanol, or oils of animal, vegetative, or synthetic origin. The pharmaceutical carrier may also contain preservatives, buffers, etc. as are known in the art.

The compounds of Formula I may be admixed with any inert carrier and utilized in laboratory assays in order to determine the concentration of the compounds within the urine, serum, etc. of the patient as is known in the art.

The following examples are presented in order to further illustrate the present invention. However, they should not be construed as limiting the scope of the invention in any manner. As used in the following examples, the following terms have the meanings indicated: "g" refers to grams, "mg" refers to milligrams, "kg" refers to kilograms, "mmol" refers to millimoles, "mL" refers to milliliters, "° C." refers to degrees Celsius, "mp" refers to melting point, "dec" refers to decomposition, "M" refers to molar.

EXAMPLE 1

This example demonstrates one of the condensation reactions of Reaction Scheme 1.
N-[4-[3-[4-(3,4-Difluorobenzoyl)piperidin-1-yl]-1-oxo-2,2-dimethylpropane]phenyl]methanesulfonamide

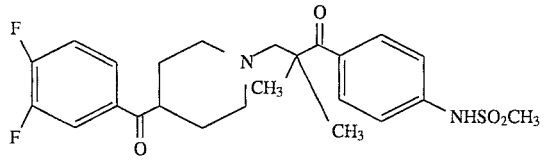

Combine 4-(3,4-difluorobenzoyl)piperidine (4.00 g, 15.3 mmol), N-[4-(1-oxo-2-methylpropane)phenyl]methanesulfonamide (3.7 g, 15.3 mmol), and paraformaldehyde (0.51 g, 16.8 mmol) in acetic acid (40 mL) and heat to reflux. After 3 hours and after 4.5 hours paraformaldehyde (0.51 g, 16.8 mmol) is added and the heating is continued. After 5.5 hours carefully pour the reaction mixture into a stirred aqueous solution of potassium bicarbonate layered with ethyl acetate. Separate the layers and extract the organic layer with a saturated solution of sodium chloride, dry over $MgSO_4$, filter, and evaporate in vacuo. Chromatograph on silica gel, eluting with 1/1 ethyl acetate/hexane and evaporate the product containing fractions to obtain an oil. Dissolve the oil in ethyl acetate (100 mL) and add 0.28M hydrogen chloride in ethyl acetate (50 mL) and collect the solid that forms. Recrystallize the solid from ethanol (75 mL) to give the title compound: mp; 194°–195° C. (dec): Elem Anal Calcd for $C_{24}H_{28}F_2N_2O_4S \cdot HCl$; C, 55.97; H, 5.68; N, 5.44: Found; C, 56.00; H, 5.64; N, 5.23.

EXAMPLE 2

This example demonstrates one of the condensation reactions of Reaction Scheme 1.
N-[4- [3-[4-(4-Fluorobenzoyl) piperidin-1-yl]-1-2,2-dimethylpropane]phenyl]methanesulfonamide

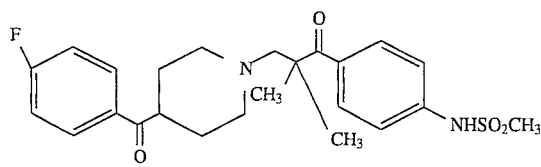

Combine 4-(4-fluorobenzoyl)piperidine (4.00 g, 16.4 mmol), N-[4-(1-oxo-2-methylpropane)phenyl]methanesulfonamide (4.0 g, 16.4 mmol), and paraformaldehyde (0.56 g, 18.6 mmol) in acetic acid (40 mL) and heat to reflux. After 3 hours and after 4.5 hours paraformaldehyde (0.51 g, 16.8 mmol) is added and the heating is continued. After 5.5 hours carefully pour the reaction mixture into a stirred aqueous solution of sodium bicarbonate. Extract the basic solution twice with dichloromethane and extract the combined organic layer with a saturated solution of sodium chloride, dry over $MgSO_4$, filter, and evaporate in vacuo. Chromatograph on silica gel, eluting with 1/1 ethyl acetate/hexane and evaporate the product containing fractions to obtain an oil. Dissolve the oil in ethyl acetate (100 mL) and add 0.56M hydrogen chloride in ethyl acetate (25 mL) and collect the solid that forms. Recrystallize the solid from ethanol (75 mL) to give the title compound: mp; 193°–194° C.: Elem Anal Calcd for $C_{24}H_{29}FN_2O_4S \cdot HCl$; C, 58.00; H, 6.08; N, 5.64: Found; C, 57.13; H, 6.15; N, 5.41.

EXAMPLE 3

This example demonstrates one of the condensation reactions of Reaction Scheme 1.
N-[4-[3-[4-(3,4-Difluorobenzoyl)piperidin-1-yl]-1-oxo-2,2 spirocyclohexylpropane]phenyl]methanesulfonamide

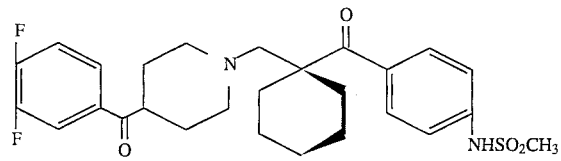

Combine 4-(3,4-difluorobenzoyl)piperidine (4.00 g, 15.3 mmol), [4-(N-methanesulfonamido)]phenyl,cyclohexylmethanone (3.7 g, 15.3 mmol), and paraformaldehyde (0.51 g, 16.8 mmol) in acetic acid (40 mL) and heat to reflux. After 3 hours and after 4.5 hours paraformaldehyde (0.51 g, 16.8 mmol) is added and the heating is continued. After 5.5 hours carefully pour the reaction mixture into a stirred aqueous solution of potassium bicarbonate layered with ethyl acetate. Separate the layers and extract the organic layer with a saturated solution of sodium chloride, dry over $MgSO_4$, filter, and evaporate in vacuo. Chromatograph on silica gel. Combine with ethyl acetate (100 mL) and add 0.28M hydrogen chloride in ethyl acetate (50 mL) and collect the solid that forms. Recrystallize to give the title compound.

EXAMPLE 4

This example demonstrates one of the Friedel-Crafts reactions of Reaction Scheme 2.

N-[4-(1-Oxo-2-methylpropane)phenyl]methanesulfonamide

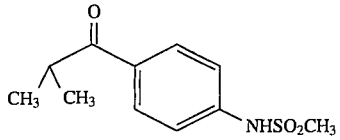

Combine N-phenylmethanesulfonamide (36.0 g, 215 mmol) and isobutyryl chloride (46 mL, 439 mmol) in dichloromethane (100 mL) and cool to −15° C. Slowly add aluminum chloride (86 g, 439 mmol) and then warm the reaction mixture to ambient temperature. After 4 hours pour the reaction mixture onto cracked ice (1 kg) containing 12M hydrochloric acid (200 mL) and stir until all the ice melts. Separate the layers and extract the aqueous layer with dichloromethane, extract the combined organic layers with a saturated sodium chloride solution, dry over MgSO$_4$, filter, and evaporate in vacuo. Chromatograph on silica gel, eluting with 30% ethyl acetate/hexane and evaporate the product containing fractions to obtain a solid. Recrystallize the solid from isopropanol (100 mL) to give the title compound: mp; 134°–135° C.: Elem Anal Calcd for C$_{11}$H$_{15}$NO$_3$S; C, 54.76; H, 6.27; N, 5.80: Found; C, 54.90; H, 6.33; N, 5.97.

EXAMPLE 5

This example demonstrates one of the Friedel-Crafts reactions of Reaction Scheme 2.

[4-(N-Methanesulfonamido)phenyl],cyclohexylmethanone

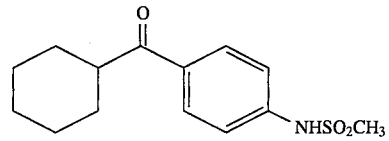

Combine N-phenylmethanesulfonamide (36.0 g, 215 mmol) and cyclohexanecarbonyl chloride (58.7 mL, 439 mmol) in dichloromethane (100 mL) and cool to −15° C. Slowly add aluminum chloride (86 g, 439 mmol) and then warm the reaction mixture to ambient temperature. After 4 hours pour the reaction mixture onto cracked ice (1 kg) containing 12M hydrochloric acid (200 mL) and stir until all the ice melts. Separate the layers and extract the aqueous layer with dichloromethane, extract the combined organic layers with a saturated sodium chloride solution, dry over MgSO$_4$, filter, and evaporate in vacuo. Chromatograph on silica gel to give the title compound.

What is claimed is:

1. The compound, N-[4-[3-[4-(4-fluorobenzoyl)piperidin-1-yl]- 1-oxo-2,2-diethylpropane]phenyl]methanesulfonamide, or a pharmaceutically acceptable addition salt thereof.

2. The compound, N-[4-[3-[4-(3,4-difluorobenzoyl)piperidin-1-yl-]-1-oxo-2,2-dipropylpropane]phenyl]methanesulfonamide, or a pharmaceutically acceptable addition salt thereof.

3. The compound, N-[4-[3-[4-(3,4-difluorobenzoyl)piperidin- 1-yl-]-1-oxo-2,2-spirocyclohexylpropane]phenyl]methanesulfonamide, or a pharmaceutically acceptable addition salt thereof.

* * * * *

UNITED STATES PATENT AND TRADEMARK OFFICE
CERTIFICATE OF CORRECTION

PATENT NO. : 5,541,201

DATED : July 30, 1996

INVENTOR(S) : Albert A. Carr, et al.

It is certified that error appears in the above-identified patent and that said Letters Patent is hereby corrected as shown below:

At column 1, line 7, the patent reads "08/71,882" and should read --08/171,882--.
At column 3, line 66, the patent reads "yl]-oxo" and should read --yl]-1-oxo--.
At column 4, line 14. the patent reads "2dimethyl" and should read --2-dimethyl--.
At column 4, line 17, the patent reads "below Reaction" and should read --below in Reaction--.
At column 4, line 59, the patent reads "an condensation" and should read --a condensation--.
At column 9, line 65, the patent reads "1-2,2" and should read --1-oxo-2,2--.

Signed and Sealed this

Fourteenth Day of April, 1998

*Attest:*

BRUCE LEHMAN

*Attesting Officer*      *Commissioner of Patents and Trademarks*